(12) United States Patent  (10) Patent No.: US 7,481,827 B2
Ryan et al.  (45) Date of Patent: Jan. 27, 2009

(54) LINKING TRANSCONNECTOR FOR COUPLING SPINAL RODS

(75) Inventors: Christopher J. Ryan, West Chester, PA (US); Thomas R. Keyer, Aston, PA (US); Martin Walther, West Chester, PA (US)

(73) Assignee: Synthes (U.S.A.), West Chester, PA (US)

( * ) Notice: Subject to any disclaimer, the term of this patent is extended or adjusted under 35 U.S.C. 154(b) by 392 days.

(21) Appl. No.: 10/684,351

(22) Filed: Oct. 9, 2003

(65) Prior Publication Data

US 2005/0080416 A1  Apr. 14, 2005

(51) Int. Cl.
*A61B 17/56* (2006.01)

(52) U.S. Cl. ........................................ 606/250; 403/56

(58) Field of Classification Search .................. 606/59, 606/61, 246, 250–260, 264–265, 270–272, 606/276–279, 330; 403/122, 123, 131, 56
See application file for complete search history.

(56) References Cited

U.S. PATENT DOCUMENTS

| 2,230,095 | A | * | 1/1941 | Van Daam ................... 392/436 |
| 2,330,095 | A | * | 9/1943 | Venditty ..................... 403/131 |
| 4,257,409 | A | * | 3/1981 | Bacal et al. .................... 606/61 |
| 4,369,770 | A | | 1/1983 | Bacal et al. |
| 4,433,677 | A | | 2/1984 | Ulrich et al. |
| 4,611,582 | A | | 9/1986 | Duff |
| 4,815,453 | A | | 3/1989 | Cotrel |
| 4,955,885 | A | | 9/1990 | Meyers |
| 4,998,936 | A | | 3/1991 | Mehdian |
| 5,005,562 | A | | 4/1991 | Cotrel |
| 5,010,879 | A | * | 4/1991 | Moriya et al. ................. 606/61 |
| 5,084,049 | A | | 1/1992 | Asher et al. |
| 5,147,360 | A | | 9/1992 | Dubousset |
| 5,154,718 | A | | 10/1992 | Cozad et al. |
| 5,209,752 | A | * | 5/1993 | Ashman et al. ............... 606/61 |
| 5,261,907 | A | | 11/1993 | Vignaud et al. |
| 5,275,600 | A | | 1/1994 | Allard et al. |
| 5,312,405 | A | | 5/1994 | Korotko et al. |

(Continued)

FOREIGN PATENT DOCUMENTS

DE  32 19 575 A1  12/1983

(Continued)

*Primary Examiner*—Eduardo C Robert
*Assistant Examiner*—James L Swiger
(74) *Attorney, Agent, or Firm*—Stroock & Stroock & Lavan LLP (57) ABSTRACT

A Linking Transconnector is disclosed for coupling a first longitudinal spinal rod to a second longitudinal spinal rod. The Linking Transconnector generally includes a pair of hook engaging members for engaging the longitudinal spinal rods, a lateral rod for spanning a distance between the hook engaging members, and a locking element which interconnects the hook engaging members with the lateral rod. The locking element being configured to allow for multiple degrees of adjustment to permit the Linking Transconnector to accommodate for varying spinal rod alignments. The locking element also permits the location of the lateral rod to be fixed relative to the hook engaging members once the desired position of the lateral rod with respect to the longitudinal spinal rods has been achieved. The locking element may also be able to fix the position of the lateral rod with respect to the hook engaging members by a force applied to the locking element.

21 Claims, 4 Drawing Sheets

U.S. PATENT DOCUMENTS

| | | | |
|---|---|---|---|
| 5,366,455 A | | 11/1994 | Dove et al. |
| 5,423,818 A | * | 6/1995 | Van Hoeck et al. ............ 606/61 |
| 5,437,671 A | | 8/1995 | Lozier et al. |
| 5,439,463 A | | 8/1995 | Lin |
| 5,476,462 A | * | 12/1995 | Allard et al. .................. 606/60 |
| 5,498,263 A | | 3/1996 | DiNello et al. |
| 5,507,746 A | | 4/1996 | Lin |
| 5,522,816 A | | 6/1996 | Dinello et al. |
| 5,527,314 A | | 6/1996 | Brumfield et al. |
| 5,531,747 A | | 7/1996 | Ray |
| 5,534,002 A | | 7/1996 | Brumfield et al. |
| 5,549,607 A | | 8/1996 | Olson et al. |
| 5,569,246 A | | 10/1996 | Ojima et al. |
| 5,575,791 A | * | 11/1996 | Lin ............... 606/61 |
| 5,601,552 A | * | 2/1997 | Cotrel .......... 606/61 |
| 5,620,444 A | | 4/1997 | Assaker |
| 5,624,442 A | | 4/1997 | Mellinger et al. |
| 5,630,816 A | | 5/1997 | Kambin |
| 5,651,789 A | | 7/1997 | Cotrel |
| 5,667,506 A | | 9/1997 | Sutterlin |
| 5,667,507 A | | 9/1997 | Corin et al. |
| 5,669,910 A | | 9/1997 | Korhonen et al. |
| 5,676,665 A | | 10/1997 | Bryan |
| 5,681,312 A | | 10/1997 | Yuan et al. |
| 5,688,272 A | | 11/1997 | Montague et al. |
| 5,693,053 A | | 12/1997 | Estes |
| 5,707,372 A | | 1/1998 | Errico et al. |
| 5,709,684 A | | 1/1998 | Errico et al. |
| 5,716,355 A | | 2/1998 | Jackson et al. |
| 5,752,955 A | | 5/1998 | Errico |
| 5,885,284 A | | 3/1999 | Errico |
| 5,899,903 A | * | 5/1999 | Cotrel .......... 606/61 |
| 5,947,966 A | | 9/1999 | Dewry |
| 5,980,523 A | | 11/1999 | Jackson |
| 5,984,923 A | | 11/1999 | Breard |
| 5,989,251 A | | 11/1999 | Nichols |
| 6,096,039 A | | 8/2000 | Stoltenberg et al. |
| 6,110,173 A | | 8/2000 | Thomas, Jr. |
| 6,113,600 A | | 9/2000 | Drummond et al. |
| 6,136,000 A | | 10/2000 | Louis et al. |
| 6,136,003 A | | 10/2000 | Hoeck et al. |
| 6,171,311 B1 | | 1/2001 | Richelsoph |
| 6,217,578 B1 | | 4/2001 | Crozet et al. |
| 6,234,705 B1 | | 5/2001 | Troxell |
| 6,238,396 B1 | | 5/2001 | Lombardo |
| 6,261,288 B1 | | 7/2001 | Jackson |
| 6,264,658 B1 | | 7/2001 | Lee et al. |
| 6,283,967 B1 | | 9/2001 | Troxell et al. |
| 6,302,882 B1 | | 10/2001 | Lin et al. |
| 6,306,137 B2 | | 10/2001 | Troxell |
| 6,328,741 B1 | | 12/2001 | Richelsoph |
| 6,355,038 B1 | | 3/2002 | Pisharodi |
| 6,402,751 B1 | | 6/2002 | Hoeck et al. |
| 6,413,258 B1 | | 7/2002 | Bernhardt, Jr. |
| 6,432,108 B1 | | 8/2002 | Burgess et al. |
| 6,524,310 B1 | | 2/2003 | Lombardo et al. |
| 6,551,318 B1 | | 4/2003 | Stahurski |
| 6,554,832 B2 | | 4/2003 | Shluzas |
| 6,562,040 B1 | | 5/2003 | Wagner |
| 6,589,243 B1 | | 7/2003 | Viart et al. |
| 6,602,253 B2 | | 8/2003 | Richelsoph et al. |
| 6,602,254 B2 | | 8/2003 | Gertzbein et al. |
| 6,616,668 B2 | | 9/2003 | Altarac et al. |
| 2001/0047171 A1 | | 11/2001 | Troxell et al. |
| 2002/0052603 A1 | | 5/2002 | Nichols et al. |
| 2002/0082599 A1 | | 6/2002 | Crandall et al. |
| 2002/0138077 A1 | | 9/2002 | Ferree |
| 2002/0143327 A1 | | 10/2002 | Shluzas |
| 2002/0169448 A1 | | 11/2002 | Vanacker .................. 606/61 |
| 2002/0169450 A1 | | 11/2002 | Lange |
| 2002/0169451 A1 | | 11/2002 | Yeh |
| 2003/0004512 A1 | | 1/2003 | Farris et al. |
| 2003/0028192 A1 | | 2/2003 | Schar et al. |
| 2003/0045874 A1 | | 3/2003 | Thomas, Jr. |
| 2003/0050640 A1 | | 3/2003 | Lee et al. |
| 2003/0083659 A1 | | 5/2003 | Lin et al. |

FOREIGN PATENT DOCUMENTS

| | | |
|---|---|---|
| DE | 43 30 837 A1 | 9/1993 |
| EP | 0 811 357 A1 | 12/1997 |
| EP | 0 813 845 A1 | 12/1997 |
| EP | 0 953 316 A1 | 11/1999 |
| FR | 2 645 427 | 4/1989 |
| FR | 2 714 590 | 1/1994 |
| JP | 2002-355252 | 12/2002 |
| WO | WO 02/38061 | 5/2002 |

* cited by examiner

LINKING TRANSCONNECTOR FOR COUPLING SPINAL RODS

FIELD OF THE INVENTION

The present invention relates to a device for spinal fixation, and in particular to a transconnector for coupling adjacent spinal rods, or other elongated members.

BACKGROUND OF THE INVENTION

It is often necessary to surgically correct and stabilize spinal curvatures, or to facilitate spinal fusion, for example as the result of a degenerative spinal disorder such as scoliosis. Numerous systems for use in spinal correction and fixation have been disclosed. These systems usually include a pair of elongated members, typically either rods or plates, longitudinally placed on the posterior spine on either side of spinous processes of the vertebral column. For the sake of simplicity, the term "rod" will be used hereafter to refer to any elongated member regardless of size and/or shape. Each rod is attached to various vertebra along the length of the spine by way of attachment devices which may include, but are not limited to, pedicle screws, plates, transverse process hooks, sublaminar hooks, pedicle hooks, clamps, wire, etc.

It is also well known that the strength and stability of such dual rod assemblies can be increased by coupling the two rods with a cross-brace or transconnector which extends substantially horizontally across the spine to connect the longitudinal spinal rods. The use of transconnectors, however, can provide surgeons with one or more difficulties. First, the simplest situation in which a transconnector could be used occurs when the two rods are parallel to each other, i.e. there is no rod convergence or divergence in the medial-lateral direction; where the two rods have the same orientation with respect to the coronal plane viewed in the anterior-posterior direction, i.e. the rods are coplanar from a lateral view; and where the two rods are located at a fixed, predetermined distance from each other. However, due to a wide variety of factors, the two rods are rarely so geometrically aligned in clinical situations.

Thus, it is advantageous to provide a transconnector which may be adjusted to adapt to variations in spinal rod alignment. The addition of such adjustability, however, may require the transconnector to consist of numerous pieces that can be difficult to assemble and use while in the surgical environment.

Furthermore, when transconnectors are placed over adjacent spinal rods, the extended profile of the device often results in soft tissue trauma and may result in surgical complications. Thus, it is advantageous to provide a transconnector with as small a lateral (i.e., transverse) profile as possible to decrease the total amount of soft tissue trauma incurred, and to minimize the chance for subsequent complications.

It is further advantageous to provide a transconnector that, once assembled, prevents disassembly of the individual pieces of the transconnector assembly, thereby helping to facilitate installation of the transconnector by reducing the likelihood that the transconnector will accidentally come apart during installation in the patient. It is also advantageous to provide a transconnector that reduces the overall number of steps required to fix the location of the transconnector with respect to the longitudinal spinal rods, thereby facilitating installation of the transconnector by reducing the time and effort needed for installation in the patient.

Thus, there exists a need for an improved transconnector for coupling adjacent spinal rods which advantageously may be adapted to adjust to varying spinal rod alignments, which has a reduced lateral footprint for reducing associated tissue trauma and which when pre-assembled will remain in tact during installation in the patient.

SUMMARY OF THE INVENTION

The present invention relates to a Linking Transconnector used for coupling a first longitudinal spinal rod to a second longitudinal spinal rod. The Linking Transconnector generally includes a pair of hook engaging members for engaging the longitudinal spinal rods, a lateral rod for spanning a distance between the hook engaging members, and a locking element which interconnects the hook engaging members with the lateral rod. The locking element generally includes a locking sleeve and a bushing, the locking sleeve being slidably located on the lateral rod thereby permitting the Linking Transconnector to accommodate varying distances between the longitudinal spinal rods, while the bushing is sized and dimensioned to be disposed between the locking sleeve and the hook engaging members thereby permitting universal adjustment between the hook engaging members and the lateral rod, and thus between the longitudinal spinal rods and the lateral rod.

In one embodiment, the locking element is configured to provide multiple degrees of adjustment including both telescoping adjustment and universal adjustment to permit the Linking Transconnector to accommodate varying spinal rod alignments including converging and/or diverging longitudinal rods, non-coplanar longitudinal rods, and longitudinal rods having varying rod separation distances.

The locking element also permits the location of the lateral rod to be fixed relative to the hook engaging members once desired position of the lateral rod with respect to the longitudinal spinal rods has been achieved. That is, the locking element may be configured to fix, both rotationally and translationally, the position of the lateral rod with respect to the hook engaging members and thus to the longitudinal spinal rods, by having both a locked and an unlocked position. In the unlocked position, the locking element may permit rotation and telescopic adjustment of the hook engaging members with respect to the lateral rod. In the locked position, the locking element may fix, both rotationally and translationally, the position of the lateral rod with respect to the associated hook engaging member, thus fixing the relative positions of the lateral rod and the longitudinal spinal rod. The locking element may be configured to the locked position through the application of a force to the locking element. This force may cause the locking sleeve to compress against the outer surface of the lateral rod while simultaneously causing the bushing to expand to engage the hook engaging members, thereby locking the relative positions of the lateral rod, the hook engaging member and the locking element both rotationally and translationally, with respect to one another.

The lateral rod and locking element may also be sized and configured to mate with the hook engaging members such that disassembly of the lateral rod and hook engaging members is prohibited once the Linking Transconnector has been assembled. This helps facilitate installation of the Linking Transconnector by reducing the likelihood that the transconnector will accidentally come apart during installation in the patient.

The present invention further relates to a transconnector for coupling first and second longitudinal spinal rods, the transconnector including a pair of hook members, each hook member having a recess for receiving one of the longitudinal spinal rods; each recess further having an axis; a lateral rod for interconnecting the hook members; and a pair of universal joints for interconnecting the hook members with the lateral rod; wherein each hook member includes a through bore having an axis for receiving a wedge member, the through bore axis being orientated substantially perpendicular to the recess axis.

The present invention further relates to a transconnector for coupling first and second longitudinal spinal rods, each spinal rod having a longitudinal axis, the transconnector including a pair of hook members, each hook member having a recess for receiving one of the longitudinal spinal rods and a through bore having an axis for receiving a wedge member, the through bore being orientated substantially perpendicular to the axis of the longitudinal spinal rod; a lateral rod for interconnecting the hook members; and a pair of locking elements for interconnecting the hook members with the lateral rod; wherein the locking element has an unlocked configuration in which the locking element may move, and a locked configuration in which the locking element is fixed.

The present invention further relates to a transconnector for coupling first and second longitudinal spinal rods, each spinal rod having a longitudinal axis, the transconnector including a pair of hook members, each hook member having a recess for receiving one of the longitudinal spinal rods and a through bore having an axis for receiving a wedge member, the through bore being orientated substantially perpendicular to the axis of the longitudinal spinal rod; and a lateral rod for interconnecting the hook members; the lateral rod including a pair of locking elements one located at either end of the lateral rod for connection to the hook members; the locking elements being sized and configured to provide universal movement between the hook members and the lateral rod; wherein the locking element has an unlocked configuration in which the locking element may move, and a locked configuration in which the locking element is fixed.

The locking element of the present invention may include a locking sleeve and a bushing wherein the locking sleeve has a first end, a second end, and a through bore extending therethrough, the through bore being sized and configured to receive the lateral rod therein. Similarly, the bushing has a first end, a second end, and a through bore therethrough, the through bore being sized and configured to receive the locking sleeve therein. The bushing may be sized and configured to be slidably moveably along the locking sleeve. The locking sleeve and bushing may also include a slit therethrough for facilitating installation. The hook engaging members, locking sleeve and lateral rod may also be sized and configured so that, once assembled, the hook engaging member will not separate from the bushing, the bushing will be retained on the locking sleeve and the locking sleeve will be retained on the lateral rod. This arrangement ensures that once the Linking Transconnector has been pre-assembled it will remain intact during installation in the patient.

In use, the Linking Transconnector may be provided pre-assembled, such that a hook engaging member and locking element are provisionally attached to each end of a lateral rod. Although, the Linking Transconnector may be provided in a pre-assembled form, the lateral rod and hook engaging members may be still rotationally and translationally adjustable relative to one another. Next, the pre-assembled Linking Transconnector is installed between a pair of longitudinal spinal rods by placing the Linking Transconnector at the desired location between the spinal rods. The Linking Transconnector is then adjusted, both rotationally and translationally, until its desired position is achieved. Once achieved, the wedge members in the hook engaging members may be tightened to lock the hook engaging members to the spinal rods. Thereafter, a tool is used to engage the locking element so that the locking sleeve and bushing are moved toward each other. This causes the locking sleeve to slide within the bushing, which in turn causes increased interference between the outer surface of the locking sleeve and the inner surface of the bushing. This interference causes the locking sleeve to compress and the bushing to expand, thereby fixing the position of the locking sleeve to the lateral rod, the bushing to the hook engaging member, and the locking sleeve to the bushing.

BRIEF DESCRIPTION OF THE DRAWINGS

FIG. 5b is a lateral cross-sectional view of the locking sleeve shown in FIG. 5a.

FIG. 5c is a detailed view of the locking sleeve shown in FIG. 5a.

FIG. 6b is a cross-sectional view of the bushing shown in FIG. 6a.

DESCRIPTION OF THE PREFERRED EMBODIMENTS

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates.

The Linking Transconnector 10 may be used for coupling a first longitudinal spinal rod to a second longitudinal spinal rod. The first and second longitudinal spinal rods may be cylindrical rods, rectangular bars, plates, or any other device appropriate for use in connecting two or more adjacent vertebral bodies to facilitate spinal fixation. For the sake of simplicity, the term "rod" will be used herein to refer to any elongated member regardless of size and/or shape. In use, the first and second longitudinal spinal rods extend along the posterior spine on either side of spinous processes of the vertebral column. The first and second longitudinal spinal rods may be attached to various vertebral elements along the length of the spine by any attachment device known in the art including, but not limited to, pedicle screws, plates, transverse process hooks, sublaminar hooks, pedicle hooks, clamps, wire, etc.

The Linking Transconnector 10 may be manufactured from any material suitable for orthopedic applications including, but not limited to, stainless steel, titanium, titanium alloy, polymers, memory shaped alloys, etc.

Figures 1, 2:
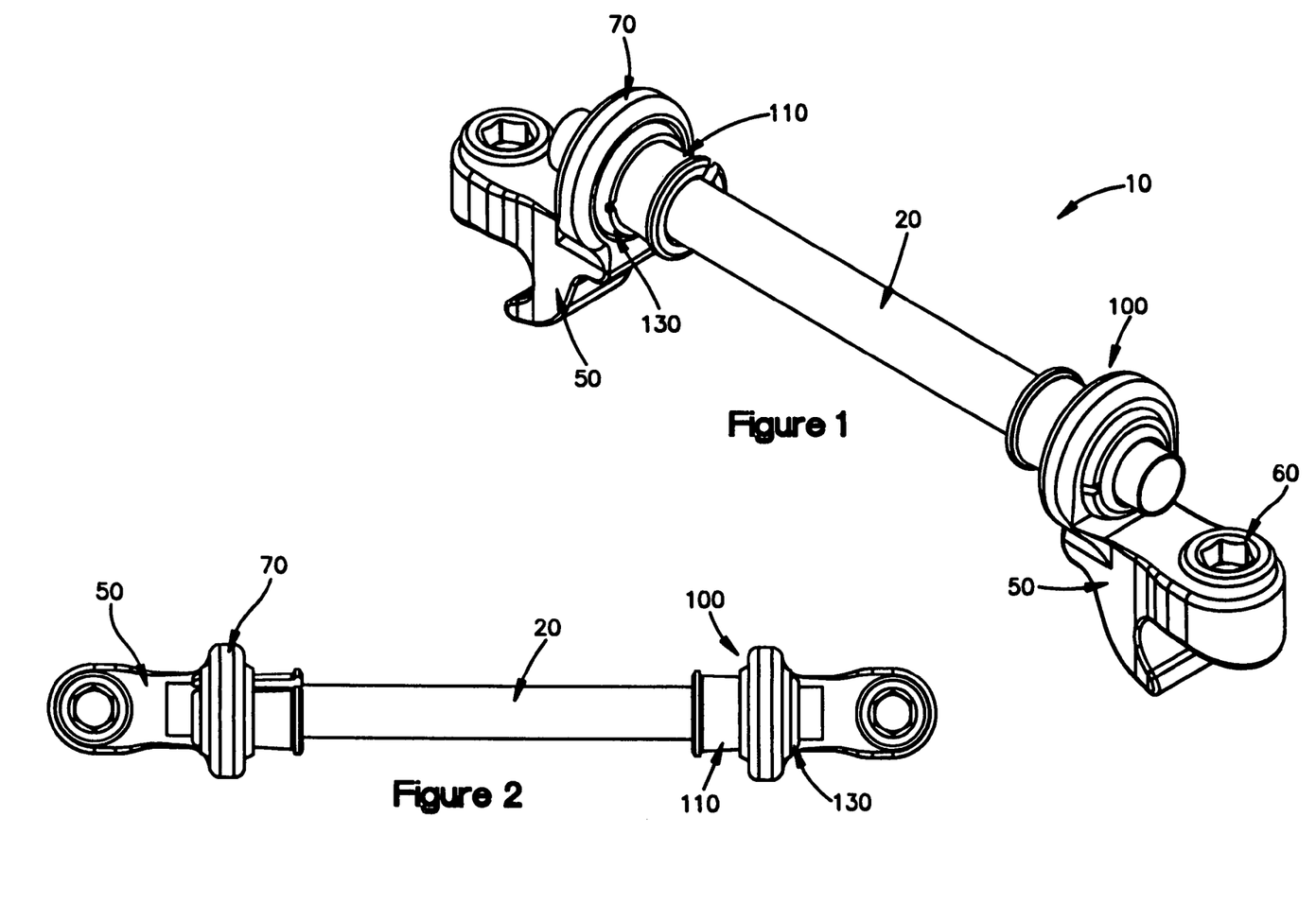
FIG. 1 is a perspective view of the Linking Transconnector according to one embodiment of the present invention.
FIG. 2 is a top view of the Linking Transconnector shown in FIG. 1.
Figure 3:
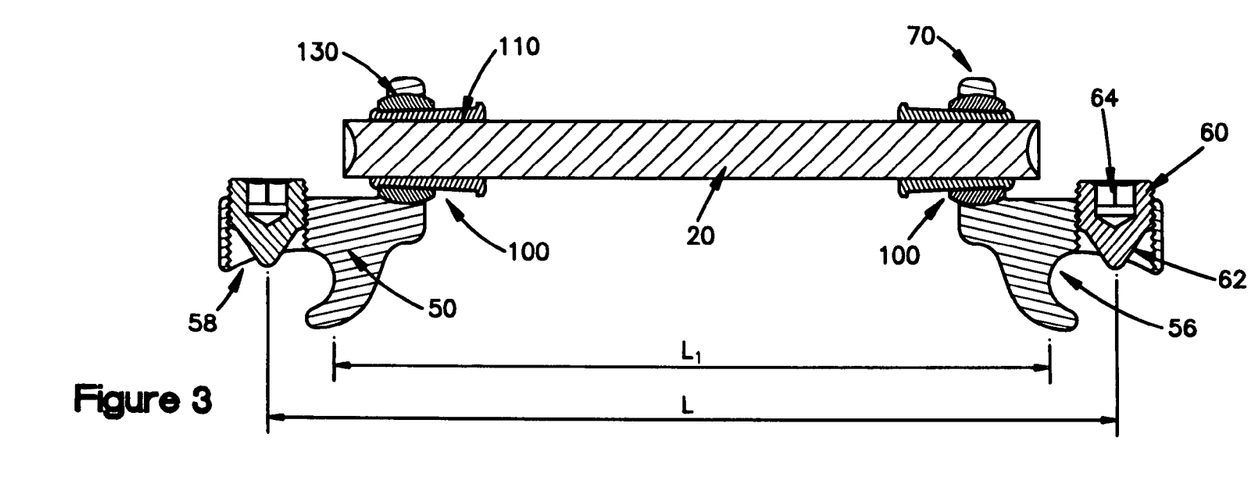
FIG. 3 is a side cross-sectional view of the Linking Transconnector shown in FIG. 1.

As shown in FIGS. 1 through 3, the Linking Transconnector 10 generally includes a pair of hook engaging members 50 for engaging the longitudinal spinal rods (not shown), a lateral rod 20 for spanning a distance between the hook engaging members 50, and a pair of locking elements 100 which interconnect the hook engaging members 50 with the lateral rod 20. Each hook engaging member 50 may include a hook recessed wall 56 for receiving one of the longitudinal spinal rods, a through bore 58 for receiving a wedge member 60 for securing the longitudinal spinal rod into engagement with the hook recessed wall 56, and a lateral rod engaging portion 70 for receiving the lateral rod 20 therethrough.

The locking element 100 may be configured to provide multiple degrees of freedom to permit the Linking Transconnector 10 to accommodate varying spinal rod alignments. In one embodiment, the locking element 100 permits the lateral rod 20 to angulate and translate with respect to at least one of the hook engaging members 50, thus permitting the Linking Transconnector 10 to accommodate, for example, converging and/or diverging longitudinal rod pairs, non-coplanar longitudinal rod pairs, and longitudinal rods having varying rod separation distances. That is, the locking element 100 generally includes a locking sleeve 110 and a bushing 130. The locking sleeve 110 may be sized and configured to be slidably positionable along the length of the lateral rod 20 thereby permitting the Linking Transconnector 10 to accommodate varying distances between longitudinal spinal rods. The bushing 130 may be sized and configured to be positioned between the locking sleeve 110 and the lateral rod engaging portion 70 thereby permitting the lateral rod 20 to be universally adjustable with respect to the hook engaging members 50, and thus the lateral rod 20 is universally adjustable with respect to the longitudinal spinal rods.

The locking element 100 also may provide for the fixation of the lateral rod 20 with respect to the longitudinal spinal rods once desired positioning of the lateral rod 20 has been achieved. That is, the locking element 100 may be configured to have both locked and unlocked positions. In the unlocked position, the locking element 100 may permit rotation and telescopic adjustment of the hook engaging members 50 with respect to the lateral rod 20. In the locked position, the locking element 100 may fix, both rotationally and translationally, the position of the lateral rod 20 with respect to the associated hook engaging member 50, thus fixing the relative positions of the lateral rod 20 and the longitudinal spinal rod. The locking element 100 may be configured to the locked position through the application of a force to the locking element 100. This force may cause the locking sleeve 110 to compress against the outer surface of the lateral rod 20 while simultaneously causing the bushing 130 to expand to engage the hook engaging members 50, thereby locking the relative positions of the lateral rod 20, the hook engaging member 50 and the locking element 100 both rotationally and translationally, with respect to one another.

The lateral rod 20 and locking element 100 may be sized and configured to prevent disassembly of the lateral rod 20 from the hook engaging members 50 once the Linking Transconnector 10 has been assembled. The lateral rod may be swaged, or flared, at both ends, and the swaged or flared portion may have a diameter greater than the unexpanded inner diameter of the locking element 100, thereby preventing the locking element 100 from sliding off the end of the lateral rod 20. This feature helps facilitate installation of the Linking Transconnector 10 during surgery by reducing the chance that the transconnector will accidentally come apart during installation in the patient.

Figure 4:
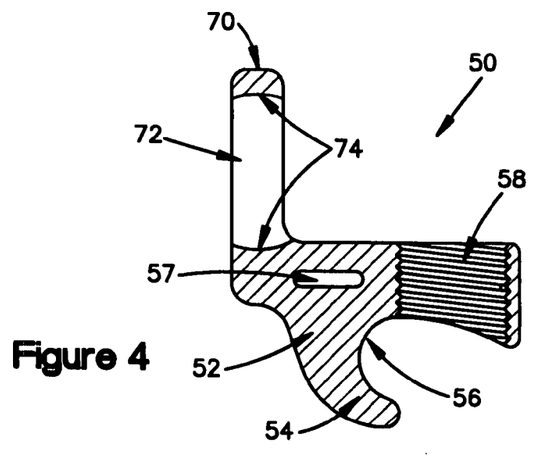
FIG. 4 is a detailed view of the hook engaging member of the Linking Transconnector shown in FIG. 1.

As best shown in FIG. 4, each hook engaging member 50 may include a body 52 having a hook 54 extending therefrom, the hook 54 having a hook recess wall 56 for receiving a longitudinal spinal rod. The hook recess wall 56 may be sized and configured such that the radius of the hook recess wall 56 conforms to the radius of the associated longitudinal spinal rod to which it will be fixed. However, the hook recess wall 56 may have a radius that is larger or smaller than the radius of the longitudinal spinal rod, as appropriate.

As shown, the hook engaging member 50 preferably has a hook recess wall 56 which is positioned laterally inboard from the center of the longitudinal spinal rods. In addition, the hook engaging member 50 may also include a through bore 58 for receiving a wedge member 60, the through bore being positioned laterally outboard from the center of the associated longitudinal spinal rod. The through bore 58 may have a longitudinal axis which is orientated substantially perpendicular to the longitudinal axis of the spinal rod. The wedge member 60 may secure the position of the longitudinal spinal rod relative to the hook engaging member 50 once desired positioning of the lateral rod 20 has been achieved.

This configuration of hook recessed wall 56 and through bore 58 may be such that when the wedge member 60 is rotated so that a bearing surface 62 of the wedge member 60 engages the longitudinal spinal rod, further rotation of the wedge member 60 may cause the longitudinal spinal rod to be urged laterally inwards (i.e., towards the centerline of the patient's spine) into lateral contact with the hook recess wall 56 which is located laterally inboard of the longitudinal spinal rod. This enables the Linking Transconnector 10 to utilize a hook 54 which contacts a reduced portion of the circumference of the longitudinal spinal rod. In one embodiment, this configuration of hook recess wall 56 and through bore 58 includes a hook 54 which extends around, and contacts, approximately 60° to 180°, preferably approximately 90° of the circumference of the longitudinal spinal rod. Thereby helping to decrease the amount of soft tissue trauma that may be incurred during installation of the transconnector. This is because the overall size of the hook engaging member 50 of the present invention may be reduced as compared to hook engagement members having wedge member through bores that are located medially, i.e., laterally inboard of the longitudinal spinal rods, and which must be used with hook engaging members located laterally outboard of the longitudinal spinal rods. The reduced lateral footprint of this design helps decrease the amount of patient soft tissue trauma generally associated with transconnector installation. Alternatively, the hook recessed wall 56 may take on any appropriate shape and configuration. For example, the hook recess wall 56 may be configured to contact the longitudinal spinal rod up to 360° around the rod's outer circumference (in which case, the hook recessed wall 56 could include a bore sized to receive the longitudinal spinal rod, and the spinal rod would be fed into and through the bore).

The reduced-contact configuration of through bore 58 and hook design makes the Linking Transconnector 10 particularly well adapted for use in the cervical region of the spine where little room for spinal fixation components exists. However, as will be appreciated by those skilled in the art, the Linking Transconnector 10 may also be used to connect longitudinal spinal rods placed in other regions of the spine including the thoracic and lumbar regions.

The hook engaging members 50 may also include one or more tool engagement recesses 57 for receiving a gripping instrument, such as forceps. The tool engagement recesses 57 may be configured to receive the jaws of a forceps, thereby allowing the Linking Transconnector 10 to be installed and/or manipulated in the patient using forceps engaged with hook engagement members 50. The tool engagement recesses 57 preferably are positioned to allow the surgeon to grip the hook engagement members 50 from above, to provide for maneuvering of the Linking Transconnector 10 into position on the vertebra from above, or outside of the patient. The tool engagement recesses 57 may be formed on each side of the hook engaging members 50, and they may extend entirely across the outer surface of the hook engaging members 50 or only along a portion thereof. It should be noted however that the tool engagement recesses 57 are not limited to the elongated slots as shown and that other configurations are contemplated. The tool engagement recesses 57 and instrument jaws may have any mating configuration that allows the instrument to securely grasp the hook engaging members 50. When used with an instrument such as forceps, the tool engagement recesses 57 may provide sufficient grip on the hook engaging members 50 for a surgeon to maneuver the hook engaging members 50 into position through obstructions such as ligaments and other tissues.

Additionally, the tool engagement recesses 57 are preferably positioned at a sufficient distance and/or orientation with respect to the hook recessed wall 56 to allow the longitudinal spinal rod to be inserted into the hook recessed wall 56 while the tool engagement recesses 57 are engaged by an instrument. In other words, the tool engagement recesses 57 are preferably not located in a position in which the instrument blocks access to the hook recessed wall 56 when the instruments is engaged with the tool engagement recesses 57. The tool engagement recesses 57 may also be positioned at a sufficient distance and/or orientation with respect to the wedge member 60 and locking member 100 to allow the wedge member 60 and locking member 100 to be manipulated by the surgeon while the tool engagement recesses 57 are engaged by an instrument. The tool engagement recesses 57 may also be located on other components of the transconnector such as for example, the lateral rod 20.

The wedge member 60, as shown in FIG. 3, may include, but not be limited to, a set screw, a quarter turn cam, etc. Any appropriate locking structure is contemplated which will allow the hook engaging member 50 to be fixed to the longitudinal rod. The wedge member 60 may have a bearing surface 62 shaped and configured to conform with the outer surface of an associated longitudinal spinal rod. The wedge member 60 may also have a tool engaging surface 64 configured to accept a conventional driving tool, such as, for example, a screwdriver, ratchet, etc. The tool engaging surface 64 may include, but not be limited to, an internal hex, an external hex, a torque, a star, etc.

The hook engaging members 50 may each include a means for receiving and securing the lateral rod 20, thereby enabling the hook engaging members 50 to interconnect the lateral rod 20 with the longitudinal spinal rods. The means for receiving the lateral rod may include, for example, a crimping mechanism which may receive the lateral rod 20 therein, and once the desired positioning of the lateral rod 20 is achieved, a force may be applied to the crimping mechanism thereby fixing the position of the lateral rod 20 with respect to the hook engaging members 50. Alternatively, the means for receiving the lateral rod may include a bore for receiving a tapered surface, whereby moving the tapered surface laterally with respect to the bore 70 fixes the location of the hook engaging members 50 with respect to the lateral rod 20. Furthermore, the means for receiving the lateral rod may include a bore utilizing a wedge member (i.e., a set screw), whereby once the desired positioning of the lateral rod 20 is achieved, rotation of the wedge member fixes the position of the lateral rod 20 with respect to the hook engaging members 50. Also the means for receiving the lateral rod may include a top loading U-shaped member having an external threaded surface for receiving a locking nut, whereby once the desired positioning of the lateral rod 20 is achieved, rotation of the locking nut fixes the position of the lateral rod 20 with respect to the hook engaging members 50.

In one embodiment, the means for receiving the lateral rod 20 includes a lateral rod engaging portion 70 having an opening 72 sized and configured to receive the lateral rod 20 and the locking element 100. The opening 72 may have an inner concave surface 74 for adjustably receiving the outer convex surface of the locking element 100, thus providing a spherical adjustment assembly. Alternatively, the opening 72 may have an inner convex surface for adjustably receiving the outer concave surface of the locking element 100. This spherical adjustment configuration permits the lateral rod 20 to be universally adjustable with respect to each hook engaging member 50, and thus to the longitudinal spinal rods, thereby permitting the Linking Transconnector 10 to easily accommodate a wide variety of spinal rod alignments.

Although the lateral rod engaging portion 70 is described herein and shown as having an annular or circular shape, the lateral rod engaging portion 70 may take on any suitable shape for receiving the lateral rod 20 and locking element 100 including, but not limited to, oval, elliptical, etc. Preferably, the engaging surfaces of the lateral rod engaging portion 70, the lateral rod 20, and the locking element 100 all have a substantially corresponding shape.

As best shown in FIG. 3, the lateral rod 20 may be a rod having a cylindrical cross-section, and a length "$L_1$" sufficient to extend between adjacent hook engaging members 50. As will be appreciated by those skilled in the art, however, the lateral rod 20 may take on any suitable shape known in the art.

Figure 5A:
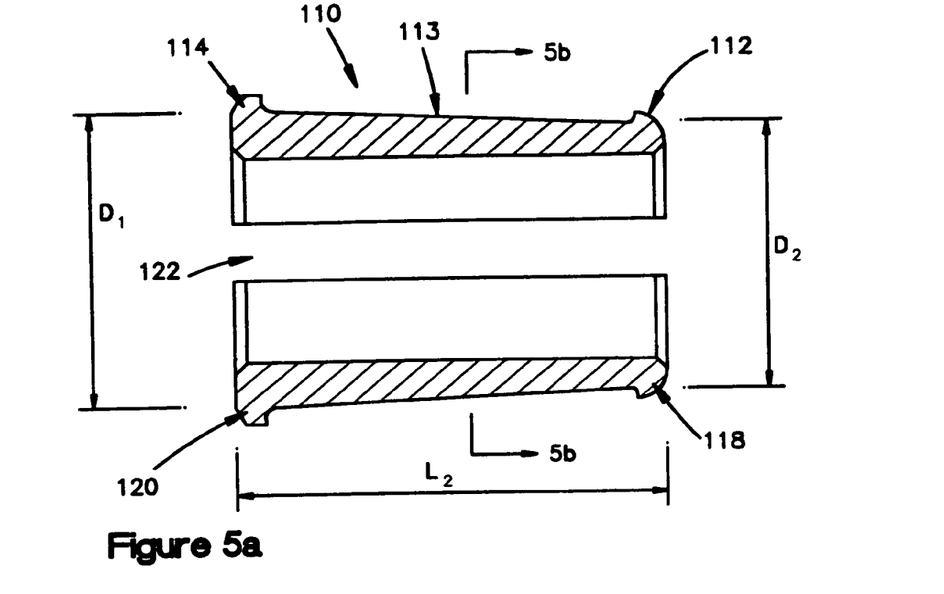
FIG. 5a is a longitudinal cross-sectional view of the locking sleeve of the Linking Transconnector shown in FIG. 1.
Figure 5B:
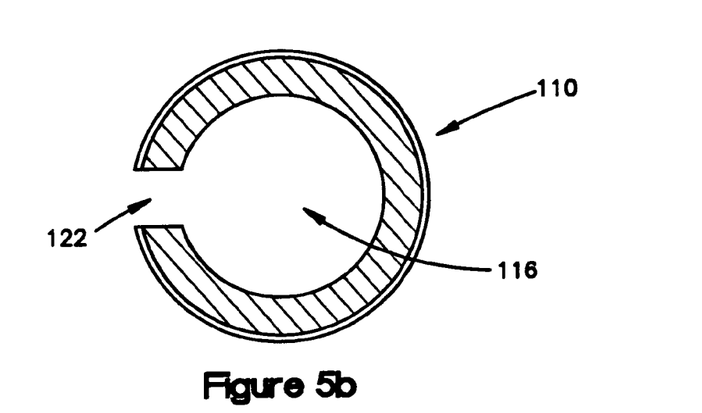
Figure 5C:
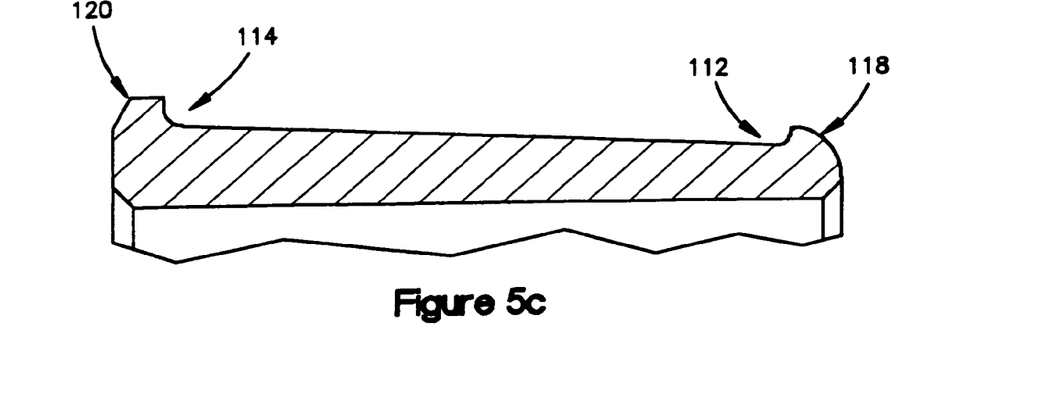

The lateral rod 20 may include a pair of locking elements 100, one located at either end of the lateral rod 20 for connection to a pair of hook engaging members 50. As shown in FIGS. 1 through 3, each locking element 100 may include a locking sleeve 110 and a bushing 130. Alternatively, however, the locking element 100 may take on other embodiments, for example, the locking element 100 may consist of only a single piece which may directly interconnect the hook engaging members 50 and the lateral rod 20. As best shown in FIGS. 5$a$ through 5$c$, the locking sleeve 110 may take the shape of a generally cylindrical member having a first end 112, a second end 114, and a through bore 116 extending therethrough. The through bore 116 preferably is sized and shaped for receiving the lateral rod 20, while the outer surface 113 of the locking sleeve 110 is sized and shaped to receive the through bore 136 of the bushing 130. More preferably, the locking sleeve through bore 116 has a size permitting receipt of the lateral rod 20 in a sliding manner thus enabling the Linking Transconnector 10 to accommodate varying distances between longitudinal spinal rods by sliding the locking elements 100 along the length of the lateral rod 20. Each end of the lateral rod 20 may have a flange (not shown) to prevent the locking sleeve 110 from sliding off the lateral rod 20 once installed thereon.

The first and second ends 112, 114 of the locking sleeve 110 may also include flanges 118, 120, respectively. The flanges 118, 120 act as stops for bushing 130, which, when installed onto the locking sleeve 110, may slide along the outer surface 113 of the locking sleeve 110. This arrangement ensures that the bushing 130 will not slide off the locking sleeve 110 once the locking sleeve 110 and bushing 130 have been assembled onto the lateral rod 20.

The locking sleeve 110 may have a tapered outer surface 113 extending from the second end 114 to the first end 112, such that the locking sleeve's outer surface diameter "$D_1$" adjacent end 114 is greater than the locking sleeve outer diameter "$D_2$" located adjacent end 112. The locking sleeve 110 also preferably includes a through wall slit 122 which extends from the first end 112 to the second end 114. The slit 122 allows the locking sleeve 110 to expand to facilitate installation of the locking sleeve 110 over the flanges 118, 120 on the ends of the lateral rod 20, and it also allows the locking sleeve 110 to contract around the lateral rod 20, such as when a force is applied to the locking sleeve 110 to fix the location of the lateral rod 20 with respect to the locking element 100.

Figure 6A:
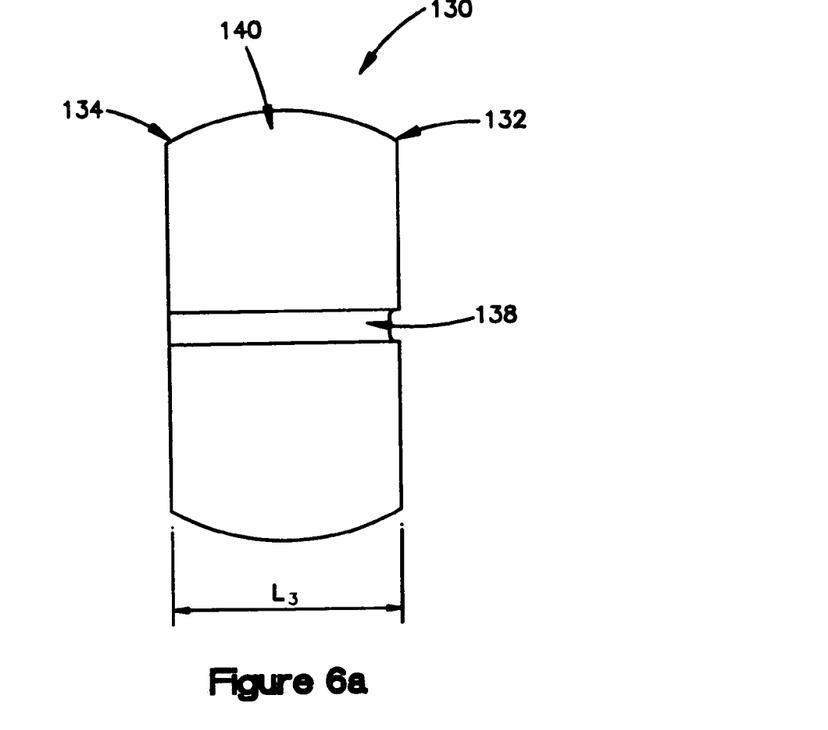
FIG. 6a is a detailed view of the bushing of the Linking Transconnector shown in FIG. 1.
Figure 6B:
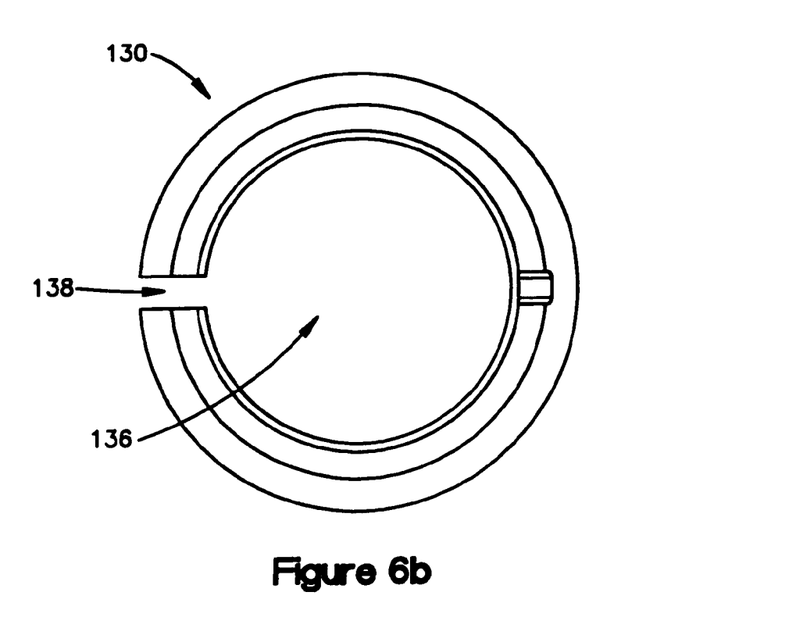

As shown in FIGS. 6a and 6b, and as previously stated, the locking element 100 also may include a bushing 130, the bushing 130 having any appropriate shape for positioning between the locking sleeve 110 and the lateral rod engaging portion 70 of the hook engaging member 50. As previously stated, the bushing 130 may have a convex outer surface for engaging with the inner concave surface of the opening 72 of the lateral rod engaging portion 70, thereby facilitating universal adjustment of the lateral rod 20 with respect to the hook engaging members 50.

The bushing 130 may include a first end 132, a second end 134 and a through bore 136 extending therethrough. The through bore 136 may be sized and shaped for receiving the locking sleeve 110 and lateral rod 20 therein. Preferably, the bushing 130 has an overall length $L_3$ shorter than the overall length $L_2$ of the locking sleeve 110 thus, as previously stated, the bushing 130 is sized and dimensioned to be slidable between flanges 112, 114 of the locking sleeve 110 so that the bushing 130 may be adjustably positionable along the length of the locking sleeve 110. The first and second flanges 118, 120 located on the first and second ends 112, 114 of the locking sleeve 110 ensure that the bushing 130 will not slid off the locking sleeve 110 during installation of the Linking Transconnector 10 in the patient.

The bushing 130 also may include a through wall slit 138 that extends from the first end 132 to the second end 134. The slit 138 allows for easy installation of the bushing 130 onto the locking sleeve 110. That is, similar to the slit 122 on the locking sleeve 110, slit 138 allows the bushing 130 to be expanded to allow its installation over flange 112 and onto the outer surface 113 of the locking sleeve 110.

In addition to facilitating installation of the individual transconnector components during assembly, the slits 122, 138 in the bushing 130 and locking sleeve 110 also allow the two pieces to be axially and rotationally locked together. That is, the outer surface 113 of the locking sleeve 110 has a diameter $D_2$ near the first end 112 which is sized to be smaller than the unexpanded through bore 136 of bushing 130, while the outer surface 113 of the locking sleeve 110 has a diameter $D_1$ near the second end 114 which is sized to be larger than the unexpanded through bore 136 of bushing 130. Thus, when the bushing 130 is positioned adjacent the first end 112 of the locking sleeve 110, the locking sleeve 110 and bushing 130 may move freely with respect to each other. However, when the bushing 130 is positioned adjacent the second end 114 of the locking sleeve 110, the larger diameter $D_2$ of the locking sleeve 110 interferes with the inner surface of the bushing 130, causing a frictional lock between the locking sleeve 110 and bushing 130. This locking action, which causes a slight compression of the locking sleeve 110 and a slight expansion of the bushing 130, also may facilitate frictional locking of the locking sleeve 110 to the lateral rod 20 and frictionally locking of the bushing 130 to the hook engaging member 50.

The outside surface of the bushing 130 may have a generally convex outer surface portion 140 extending from the first end 132 to the second end 134. This convex portion 140 may be sized and dimensioned to correspond with the inner concave surface 74 of the lateral rod engaging portion 70 so that, when assembled, the bushing 130 may slide within the concave surface, thus facilitating universal adjustment of the hook engaging member 50 relative to the lateral rod 20. Alternatively, as previously stated, the bushing 130 may have a generally concave outer surface sized and dimensioned to correspond with the inner convex surface of the lateral rod engaging portion 70. This universal adjustment permits the Linking Transconnector 10 to accommodate varying spinal rod alignments including, for example, converging or diverging spinal rods and non-coplanar spinal rods. The concave-convex configuration further assures that, once assembled, the lateral rod engaging portion 70 will not separate from the bushing 130. Since the bushing 130 is retained on the locking sleeve 110 via flanges 118, 120 and the locking sleeve 110 is itself retained on the lateral rod 20, this arrangement ensures that once it has been pre-assembled the Linking Transconnector 10 will remain intact during installation in the patient.

In one preferred embodiment, and by way of example only, the lateral rod 20 may have a diameter of about 3.5 millimeters (mm), and the locking sleeve 110 may have an overall length of about 7.3 mm and an inner diameter of about 3.5 mm for mating with the outer diameter of the lateral rod 20. The locking sleeve 100 may also have an outer diameter of 4.6 mm at the first end 112 tapering to an outer diameter of about 5.1 mm at the second end 114. The locking sleeve's first flange 118 may have an outer diameter of 4.9 mm and the second flange 120 may have an outer diameter of about 5.7 mm. The bushing 130 may have a length of about 3.5 mm and an inner diameter of about 4.7 mm for mating with the outer diameter of the locking sleeve 110. The bushing 130 also may have an outer convex surface 138 with an outer diameter of about 6.8 mm for mating with the inner surface of the lateral rod engaging portion 70 which has an inner diameter of about 6.9 mm. As will be appreciated by those skilled in the art, the dimensions of the lateral rod 20, locking sleeve 110, bushing 130, and lateral rod engaging portion 70 may be varied as appropriate and thus are not intended to be limiting.

In use, the Linking Transconnector 10 may be provided pre-assembled, such that a hook engaging member 50 and locking element 100 are provisionally attached to each end of a lateral rod 20. Although, the Linking Transconnector 10 may be provided in a pre-assembled form, the lateral rod 20 and hook engaging members 50 may be still rotationally and translationally adjustable relative to one another. That is, the locking sleeve 110 may still be free to translate along the lateral rod 20 and the spherical adjustment assembly of the bushing 130 and hook engaging member 50 permits the hook engaging member 50 to universally rotate with respect to the lateral rod 20.

Next, the pre-assembled Linking Transconnector 10 may be installed between a pair of longitudinal spinal rods by placing the Linking Transconnector 10 at the desired location between the spinal rods. The Linking Transconnector 10 is then adjusted, both rotationally and translationally, until its desired position is achieved. Once achieved, the wedge member 60 may then be tightened to lock the hook engaging members 50 to the spinal rods. Thereafter, a tool is used to engage the ends 112, 114 of the locking sleeve 110 and the outer surface of the bushing 130, and the two surfaces are moved toward each other using the tool. This causes the locking sleeve 110 to slide within the bushing 130, which, due to the increasing taper of the locking sleeve 110 causes interference between the outer surface 113 of the locking sleeve 110 and the inner surface of the bushing 130. This interference causes the locking sleeve 110 to compress and the bushing 130 to expand, thereby fixing the position of the locking sleeve 130 to the lateral rod 20, the bushing 130 to the hook engaging members 50, and the locking sleeve 110 to the bushing 130. All engagement between elements is frictional in nature, such that a reverse application of force between the bushing 130 and the locking sleeve 110 will cause the pieces to disengage such that they are again adjustable with respect to each other.

The present invention has been described in connection with the preferred embodiments. These embodiments, however, are merely for example and the invention is not restricted thereto. For example, the locking element 100 may include other embodiments. The locking element 100 may be a single piece having a tapered outer surface, configured to correspond to the inner surface of the bore 70 on the hook engaging member 50, whereby moving the locking element 100 laterally with respect to the bore 70 fixes the location of the hook engaging members 50 with respect to the lateral rod 20. Thus, it will be understood by those skilled in the art that other variations and modifications can easily be made within the scope of the invention as defined by the appended claims, thus it is only intended that the present invention be limited by the following claims.

What is claimed is:

1. A transconnector for coupling first and second longitudinal spinal rods, each spinal rod having a longitudinal axis, the transconnector comprising:
    a pair of hook members, each hook member having a recess for receiving one of the longitudinal spinal rods and a through bore having an axis, the axis of the through bore being orientated substantially perpendicular to the axis of the longitudinal spinal rod;
    a pair of wedge members, each wedge member received within the through bore formed in its respective hook member, the wedge members having locked and unlocked positions so that when in the locked position, the wedge member contacts the spinal rod located in the recess of the hook member thereby securing the position of the spinal rod with respect to the hook member;
    a lateral rod for interconnecting the hook members, the lateral rod having a first end and a second end; and
    a pair of locking elements for interconnecting the hook members with the lateral rod, each locking element comprising a locking sleeve and a bushing, the locking sleeve slidably moveable along the lateral rod, the bushing positionable between the locking sleeve and the hook member, and slidably moveable along the locking sleeve;
    wherein each locking element has an unlocked configuration in which the locking element may move relative to the lateral rod, and a locked configuration in which the locking element is fixed relative to the lateral rod.

2. A transconnector according to claim 1, wherein the lateral rod further comprises a first end, a second end, and a midpoint located therebetween, the at least one through bore being located farther from the midpoint than its associated hook recess.

3. A transconnector according to claim 1, wherein the recess is positioned laterally inboard from the axis of the longitudinal spinal rod and the through bore is positioned laterally outboard from the axis of the longitudinal spinal rods.

4. A transconnector according to claim 1, wherein at least one hook member further comprises a bore for receiving at least a portion of the lateral rod.

5. A transconnector according to claim 4, wherein the locking element further comprises an outer convex surface and the bore further comprises a corresponding inner concave surface, the two surfaces configured to be slidably engageable.

6. A transconnector according to claim 1, wherein the bushing further comprises an outer convex surface and the hook member further comprises a bore having a corresponding inner concave surface, the two surfaces configured to be slidably engageable.

7. A transconnector according to claim 1, wherein at least one hook recess has a first radius, and the associated longitudinal rod has a second radius, the first radius being substantially identical to the second radius.

8. A transconnector according to claim 1, wherein at least one wedge member has a bearing surface shaped and configured to substantially conform to the outer surface of the associated longitudinal spinal rod.

9. A transconnector according to claim 1, wherein the wedge member is selected from the group consisting of a set screw and a quarter turn cam.

10. A transconnector according to claim 1, further comprising at least one tool engagement recess formed on one of the hook members or the lateral rod.

11. A transconnector according to claim 10, wherein the at least one tool engagement recess is configured for gripping from above when the hook member or lateral rod is engaged.

12. A transconnector according to claim 10, further comprising a first tool engagement recess and a second engagement recess formed opposite the first tool engagement recess.

13. A transconnector according to claim 10, wherein the at least one tool engagement recess is configured for gripping one of the hook members or the lateral rod with a forceps.

14. A transconnector for coupling first and second longitudinal spinal rods, each spinal rod having a longitudinal axis, the transconnector comprising:
    a pair of hook members, each hook member having a recess for receiving one of the longitudinal spinal rods and a through bore having an axis, the axis of the through bore being orientated substantially perpendicular to the axis of the longitudinal spinal rod;
    a pair of wedge members, each wedge member received within the through bore formed in its respective hook member, the wedge members having locked and unlocked positions so that when in the locked position, the wedge member contacts the spinal rod located in the recess of the hook member thereby securing the position of the spinal rod with respect to the hook member;
    a lateral rod for interconnecting the hook members; and
    a pair of locking elements for interconnecting the hook members with the lateral rod, each locking element comprising a locking sleeve and a bushing; wherein:
    each locking element has an unlocked configuration in which the locking element may move relative to the lateral rod, and a locked configuration in which the locking element is fixed relative to the lateral rod; and
    the locking sleeve further comprises a first end, a second end, and a through bore extending from the first end to the second end, the through bore receiving the lateral rod therein, and the bushing comprises a third end and a forth end, and a second through bore extending from the third end to the fourth end, the second through bore receiving the locking sleeve therein.

15. A transconnector according to claim 14, wherein the bushing is sized and configured to be slidably moveable along the locking sleeve.

16. A transconnector according to claim 15, wherein the locking sleeve further comprises a first and second flange.

17. A transconnector according to claim 14, wherein the locking sleeve has a first outer diameter at the first end and a second outer diameter at the second end, the second outer diameter being greater than the first outer diameter.

18. A transconnector according to claim 14, wherein the locking sleeve further comprises a slit extending from the first end to the second end; and the bushing further comprises a slit extending from the third end to the fourth end.

19. A transconnector according to claim 14, wherein the locking sleeve and the bushing are axially and rotatably adjustable in the unlocked configuration and axially and rotationally fixed in the locked configuration.

20. A transconnector according to claim 19, wherein moving the locking sleeve along the lateral rod from a first position to a second position configures the universal joint from the unlocked to the locked position.

21. A transconnector according to claim 20, wherein moving the locking sleeve from the first to the second position further axially and rotatably locks the locking element to the lateral rod.

* * * * *